United States Patent [19]
Van Iperen

[11] Patent Number: 5,167,923
[45] Date of Patent: Dec. 1, 1992

[54] STERILITY INDICATOR

[75] Inventor: Willem H. P. Van Iperen, Westfield, N.J.

[73] Assignee: PyMaH Corporation, Fairfield, N.J.

[21] Appl. No.: 414,113

[22] Filed: Sep. 28, 1989

[51] Int. Cl.$^5$ ............................................. G01N 21/90
[52] U.S. Cl. ........................................ 422/58; 422/61; 436/1; 435/31; 435/296; 206/528; 206/530; 206/569
[58] Field of Search ................... 422/58, 61, 86, 87, 422/88; 436/1; 435/291, 292, 294, 296, 31; 206/222, 528, 530, 569

[56] References Cited

U.S. PATENT DOCUMENTS

| | | | |
|---|---|---|---|
| 3,440,144 | 4/1969 | Andersen | 435/31 |
| 3,661,717 | 5/1972 | Nelson | 435/31 |
| 4,291,122 | 9/1981 | Orelski | 435/31 |
| 4,304,869 | 12/1981 | Dyke | 435/296 |
| 4,416,984 | 11/1983 | Wheeler, Jr. | 435/31 |
| 4,461,837 | 7/1984 | Karle et aL. | 435/296 |
| 4,528,268 | 7/1985 | Andersen et al. | 435/31 |
| 4,579,823 | 4/1986 | Ryder | 435/296 |
| 4,580,682 | 4/1986 | Gorski et al. | 206/569 |
| 4,732,850 | 3/1988 | Brown et al. | 435/31 |
| 4,741,437 | 5/1988 | Gorski et al. | 206/222 |
| 4,883,641 | 11/1989 | Wicks et al. | 422/61 |

Primary Examiner—Robert J. Warden
Assistant Examiner—Laura E. Collins
Attorney, Agent, or Firm—Scully, Scott, Murphy & Presser

[57] ABSTRACT

A sterility indicator of the type used in hospitals and laboratories. The device uses a cylindrical ampule holder with an ampule containing nutrient media and spore strip disposed therein. One or more gas pervious, liquid impervious tortuous paths lie between the interior and exterior of the ampule holder. Fracturing of the ampule is by the combination of a rotation and rotation prevention means with respect to the cylindrical axis.

33 Claims, 3 Drawing Sheets

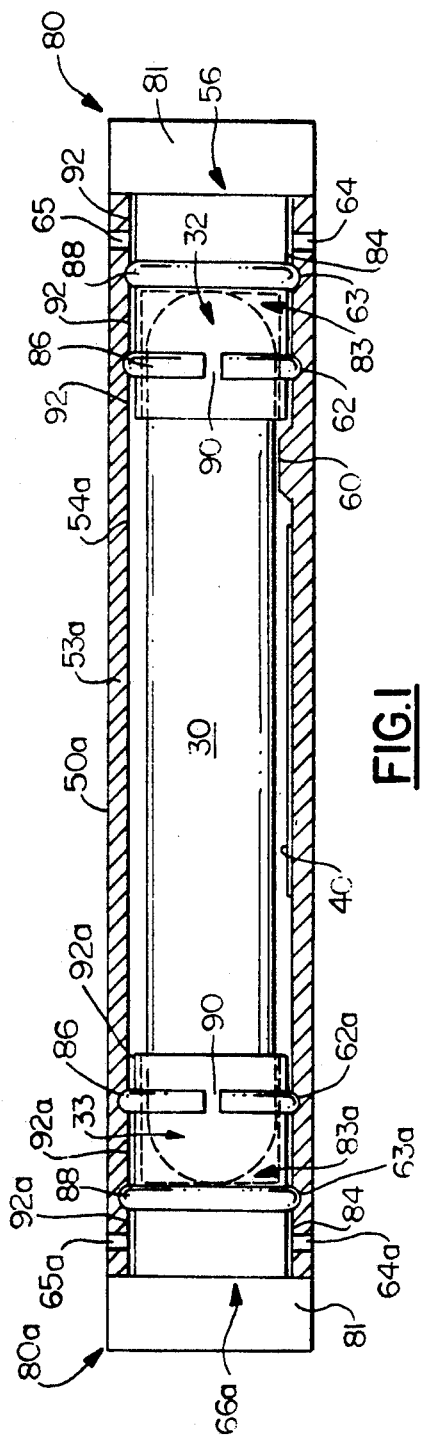
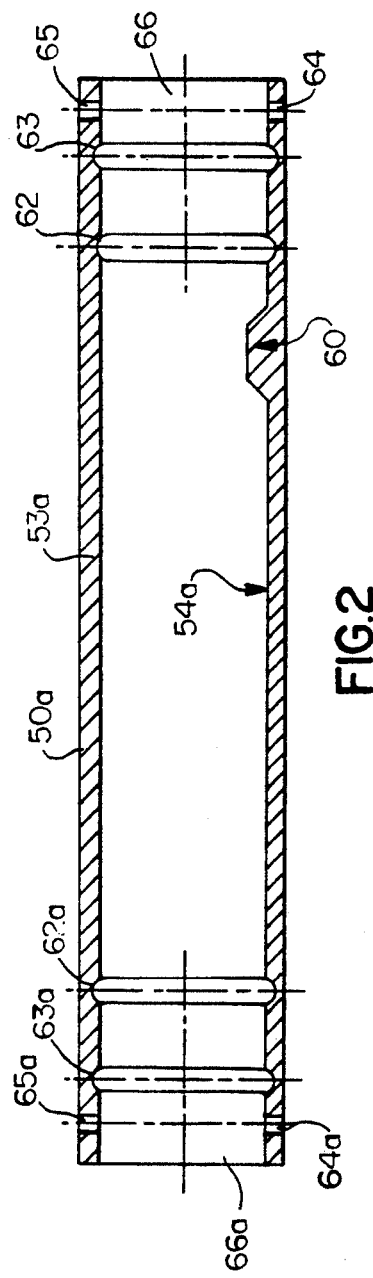

STERILITY INDICATOR

BACKGROUND OF THE INVENTION

1. Field of the Invention

The present invention is of a sterility indicator, also known as a biological indicator. The invention has application in hospitals, laboratories, etc., where sterilized equipment is necessary.

2. Discussion of the Prior Art

Sterility indicators have been used for many years in hospitals and other environments where utensils and equipment free from spores and microorganisms are required to prevent infection, the spreading of viruses, etc. Even disposable surgical utensils must be sterilized before they are packaged.

Of course, it is impossible to tell whether a utensil is sterile simply by looking at it. What is less obvious is the fact that all but the most prolonged exposure of utensils to a sterility cycle gives an acceptable probability of adequate sterilization. For "quicker" sterilization cycles, the percentage of unsterile results becomes intolerable. Subjecting all utensils requiring sterilization to prolonged cycles is inefficient, uneconomical, and time consuming. Sterility indicators were developed to allow the widespread use of "quick" sterilization cycles since their use indicates whether a sterilization cycle has been successful or not.

The prior art has developed a number of compact, disposable sterility indicators. These indicators usually come in a sealed unit which is subjected along with the utensils to a sterility cycle. The sterility cycle may be a steam cycle or an ethylene oxide (EO) cycle, all known to the art. After the cycle, the indicator is treated, resulting in an indication of whether the cycle was successful In a gravity steam sterilization cycle, steam diffuses throughout the sealed compartment in which the items to be sterilized are placed. In a vacuum steam cycle, air is evacuated from the compartment before the steam is pumped into the compartment; the evacuation and pumping may be repeated several times prior to the sterilization cycle. The vacuum eliminates the local pockets of air in the compartment which resist steam penetration in the gravity methods Wet steam more effectively kills microorganisms than dry steam, so the relative humidity (RH) of the steam cycles is usually 100%. Other variables effecting the efficacy of a steam cycle are time, temperature and whether vacuum techniques are used. For a gravity cycle at 121° C., typically the instruments are exposed for a minimum of 15 minutes. For the so called "flash" gravity cycle, instruments are typically exposed for 3 minutes at a minimum of 132° C.

In the EO cycles, air is typically removed from the chamber prior to introduction of the gas or gas mixture. EO cycles are dependent on time, concentration, RH, and temperature. For a concentration of 1200 mg/liter EO at 25° C., 1 atm and 60% RH, the instruments are typically exposed for several hours depending on the load, content and size.

A typical biological sterility indicator has a hollow outer compartment with viable microorganisms disposed therein. Disposed within a frangible inner compartment and isolated from the spores is a nutrient medium which spurs growth of the spores when the device is actuated and some type of means to indicate the growth of microorganisms. The outer compartment generally has some mechanism whereby a gas may pass into the outer compartment. Therefore, the gas or steam of a sterilization cycle may pass into the interior of the outer compartment to kill the microorganisms during the sterilization cycle.

For sterility indicators which will be subjected to a steam cycle, the spores are usually *Bacillus stearothermophilus* since they have been demonstrated to be most resistant to steam sterilization. They usually reside the spores are usually *Bacillus subtilis*, and reside on strips with $10^6$ or more spores In principle and in operation the sterility indicator is subjected to the same sterilization cycle as the utensils. The gas or steam of the cycle passes into the interior of the outer compartment, thus theoretically exposing the spores to the same sterilizing medium as any on the utensils. After the sterilization cycle, the nutrient medium is brought into contact with the spores by actuation of a mechanism which shatters the frangible inner compartment, thereby releasing the nutrient medium. The sterility indicator is then subjected to an incubation process. Any spores which survived the sterilization cycle will grow and be revealed by the indicating means. Naturally such an indication means an unacceptable sterilization cycle, while lack of an indication means the opposite.

The nutrient medium for both types of spores may be Tryptic Soy broth The detection mediums may be Bromthymol blue or purple, which change color in acidic conditions, i.e. upon growth of spores.

Incubation requires high humidity to retard drying of the spores, which retards the growth of those that survive the cycle. Typically the indicator is incubated for 24 hours and checked for a color change indicating growth. If there is no sign of growth, the indicator is incubated another 24 hours and again checked for growth.

U.S. Pat. No. 3,661,717 to Nelson exemplifies a particular embodiment of a sterility indicator. The outer compartment is a hollow cylinder with one closed end and one open end. The outer compartment is made of translucent, deformable plastic Disposed within the outer compartment is a closed cylindrical inner compartment made of frangible glass and containing the nutrient medium. Also disposed in the outer compartment is a strip with a predetermined number of viable microorganisms, and a material which indicates the growth of microorganisms through a color change. The open end of the outer compartment is closed with a liquid impervious, gas pervious sheet. Thus, the gas or steam of a sterilization cycle permeates through the sheet to the interior of the outer compartment, exposing the microorganisms on the strip to the same sterilization cycle as any microorganisms on the utensils. When the cycle is complete, any gas inside the outer compartment diffuses or is evacuated out through the sheet.

Once the cycle is complete, the frangible glass of the inner compartment is fractured by squeezing the walls of the outer compartment, thus exposing the strip to the nutrient medium. The liquid nutrient medium remains inside the outer compartment due to the sheet being liquid impervious. The unit is then incubated, and any color change in the detecting material caused by the growth of microorganisms is seen through the translucent walls of the outer compartment.

One disadvantage of this prior art device is the method of fracturing the inner compartment. To be deformable and translucent, the plastic walls of the outer compartment have to be relatively thin and, when squeezed, are susceptible to piercing by the fracturing glass of the inner compartment. This at times leads to injury to the operator as well as contamination of a sterile environment.

Another disadvantage of this prior art system is its propensity to give false negative readings. The combination of the sheet barrier and the deformable plastic walls of the outer compartment result in the strip having a longer exposure time to the gas of a sterilization cycle. Specifically, the sheet acts to some degree as a barrier to trap gas inside the outer compartment when the cycle is complete. Furthermore the plastic walls of the outer compartment absorb gas during the cycle, and release gas to the interior of the compartment during the incubation cycle. The longer exposure of the strip to the gas may result in the spores on the strip being killed while those on the utensils of interest are not. Therefore, the prior art device would indicate a successful sterilization cycle when in fact it was not.

A number of embodiments too numerous to mention attempt to solve the above problems inherent in this prior art device. A sampling of the devices can be found in U.S. Pat. Nos. 4,741,437, 4,416,984, 4,732,850, 4,461,837, 4,304,869, and 4,580,682. Many of these embodiments substitute safe but complex configurations for the relatively simple, and thus economical, inner and outer compartments of the prior art device. Some embodiments use a capsule shaped inner compartment similar to the prior art device, combined with a cylindrical outer compartment. The outer compartment in some way collapses along the cylindrical axis, thus crushing the inner compartment. Such a configuration is also inherently flawed since it attempts to break the inner compartment by applying pressure primarily along its cylindrical axis, the axis most resistant to fracture The later embodiments also attempt to correct the false positive problem By making devices with outer compartments that collapse along the cylindrical axis to open the inner compartment, the outer compartment can be made of rigid material. This material does not absorb gas to the degree that the deformable plastics of the prior art devices do. However, these methods are disadvantageous because of their complexity and resulting cost, as detailed above.

Some of the later embodiments also attempt to correct the false positive problem by replacing the gas transmissive, liquid impervious sheet with another mechanism for exposing the spores to the sterility cycle. One mechanism is a "tortuous path." The tortuous path is broadly defined as an unobstructed passage between the exterior and interior of the outer compartment having a minimum of two 90° bends in either path. The passage is "unobstructed" only in the sense that an object need not be passed through to move between the outside and inside of the outer compartment. The path is "tortuous" because it may twist around objects and physical projections in moving between the interior and exterior of the outer compartment. By substituting a tortuous path for a gas permeable sheet, the level of gas or steam inside the outer compartment is more reflective of the level outside the outer compartment at all phases of the cycle.

One problem with the prior art methods using the tortuous path is that many of those tortuous paths are not liquid impermeable. Thus when the inner compartment is accidently opened during shipping, handling or a sterility cycle, nutrient medium can leak to the outside of the sterility indicator. Considering that the nutrient medium is to spur the growth of microorganisms, such an occurrence in a hospital or clean environment is undesirable and detrimental to the future performance of the indicators.

Another problem with the prior art methods using the tortuous path was the propensity to give false positive results in the gravity steam or EO cycles. Because the prior art devices used only one tortuous path, the sterility medium was prevented from diffusing inside due to air trapped therein. As a result the spores on the strip were not exposed and killed, and the indicator after incubation would indicate growth for what may have been a successful cycle.

SUMMARY OF THE INVENTION

The present invention overcomes the disadvantages of the prior embodiments. In the present invention, a unitary sterility indicator comprises an ampule holder or, equivalently, an outer compartment, with an interior cavity and at least one opening between the interior and exterior of the ampule holder. The ampule holder is made of rigid, translucent and gas and liquid impervious material. A closed ampule, or inner compartment, containing at least the aqueous component of a nutrient medium, has dimensions which allow its at least partial reception within the ampule holder through the opening. The ampule is pressure openable and is at least partially disposed within the ampule holder. Also disposed within the ampule holder is a sample strip containing a predetermined number of spores, the portion of the nutrient medium not present in the ampule, and detector material which changes colors in response to the growth of microorganisms.

The opening of the ampule holder is closed with a closing means, which is also liquid and gas impervious. The closing means also encompasses any portion of the ampule not disposed inside the ampule holder. However, there remains a liquid impervious, gas pervious tortuous path between the interior and exterior of the closed ampule holder.

There is also a means for preventing rotation of the disposed ampule with respect to the ampule holder, as well as a means for applying a rotational force to the ampule with respect to the ampule holder from the exterior of the ampule holder.

In operation, the tortuous path allows for exposure of the sample strip to the gas or steam of the sterilization cycle, as well as providing the exit for the gas or steam when the cycle is complete. Once complete, the ampule is opened by rotating the rotational force means, the pressure being applied to the ampule by combination of the rotational force means and the rotational motion prevention means. Release of at least the aqueous component of the nutrient medium into the interior of the ampule holder allows it to combine, if necessary, with the remaining non-aqueous portion disposed within the ampule holder. The complete nutrient medium soaks the sample strip, but is confined inside the ampule holder due to the liquid impervious nature of the tortuous path. After incubation of the sterility indicator, any growth of spores which survived the sterilization cycle is indicated by a change in color of the detection means, such change being seen through the translucent walls of the ampule holder.

In a more particular embodiment of the present invention, the ample holder is cylindrical, with at least one open end. The ampule is capsule shaped and is received in the ampule holder through the open end. The closing means is a cap with a ribbed portion which is partially received in the open end. The cap interfaces with the inner surface of the ampule holder to form a gas pervious, liquid impervious tortuous path between the interior and exterior of the ampule holder. The partially received cap and the ampule holder have coaxial cylindrical axes, and the cap may be rotated with respect to the ampule holder about the axis. The received portion of the cap interfaces with the ampule. Therefore, the rotatable cap provides the means for rotating the ampule with respect to the ampule holder. Finally, a projection or fracture pad rising from the inner surface of the ampule holder provides the rotation prevention means for the ampule.

In a preferred embodiment of the invention, two tortuous paths are used at each end of the cylindrical ampule holder. These multiple paths facilitate displacement of air inside the indicator during the sterility cycle, thereby overcoming the false positive problem of the prior art devices using the tortuous path.

The above embodiment of the present invention points out its many advantages over the prior art:

The walls of the ampule holder need not be deformed to open the ampule, thus avoiding the problem of piercing the ampule holder.

The cylindrical ampule fractures much easier by applying a rotational force about its cylindrical axis, thus providing an advantage over prior art methods which attempted to crush the ampule along its cylindrical axis.

The above described embodiment has a simple configuration, and is therefore cheaper to manufacture and assemble than the relatively complex prior art devices.

The present invention uses a tortuous path, thereby lessening the percentage of false positive results over prior art devices.

The tortuous path is liquid impervious, thus preventing spillage when the ampule is prematurely broken.

Furthermore, when the sterility indicator of the present invention uses a cylindrical ampule holder with two open ends and two caps, there may be tortuous paths at both ends of the sterility indicator. This, of course, reduces the number of false negative results since more gas or steam may pass from the inside to the outside of the ampule holder at the end of the sterilization cycle, thus exposing the strip to less residual gas or steam during incubation.

Having briefly described the sterility indicator of the present invention and some of the advantages of the particular embodiments over the prior art, it follows that the present invention provides a sterility indicator with improved reliability over the prior art which is simple and effortless to use.

The device of the present invention is also safe to use. The device has relatively simple structure and is therefore economical to manufacture and assemble.

The device furthermore prevents accidental spillage of aqueous material disposed therein.

BRIEF DESCRIPTION OF THE DRAWINGS

FIG. 1 is a composite cross-sectional and side view of one preferred embodiment of the sterility indicator of the present invention.

FIG. 2 is a cross-sectional view of the ampule holder of the sterility indicator of FIG. 1.

FIG. 5b is a view taken along the line 5b–5b of FIG. 5a.

FIG. 5c is a perspective view of the caps, elements 8, of FIG. 5a.

DETAILED DESCRIPTION

Figure 3A:
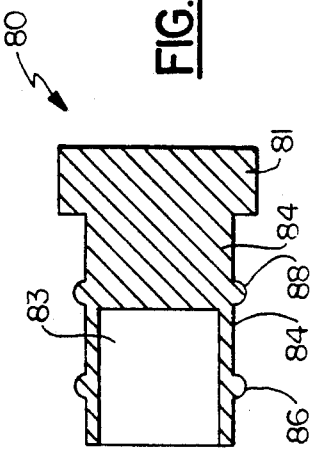
FIG. 3a is a side view of cap of the sterility indicator FIG. 1.

Referring to FIG. 1, the sterility indicator of the present invention is shown comprising ampule holder 50a, caps 80,80a and ampule 30. Ampule 30 is received completely within the interior cavity of ampule holder 50a. One end 33 of ampule 30 is received within bored region 83a of cap 80a. The other end 32 of ampule 30 is disposed inside the bored region 83 of first annular portion 84 of cap 80 when cap 80 is received in ampule holder 50a. The end 32 of ampule 30 and bored region 83 of cap 80 are represented by the dotted profile on cap 80. Similarly, the end 33 of ampule 30 and bored region 83a of cap 80a are represented by the dotted profile on cap 80a. It is seen from FIG. 1 that ampule 30 is of length such that it is supported at both ends 32,33 and does not touch the inner surface 54a of ampule holder 50a.

Cap 80 in FIG. 1 has eccentrically aligned bore 83 while cap 80a has centrically aligned bore 83a; therefore the cylindrical axis of ampule 30 is marginally tilted with respect to the mutual central axis of ampule holder 50 and caps 80,80a. When cap 80 is rotated with respect to ampule holder 50a, the central axis of bored region 83 and, consequently, the central axis of ampule 30, moves around the central axis of ampule holder 50a, resulting in ampule 30 contacting fracture pad 60. As rotation continues, the force applied to ampule 30 at fracture pad 60 and the surface of bored region 83 increases, and eventually causes the frangible glass of ampule 30 to fracture.

Attached to the inner surface 54a of ampule holder 50a is sample strip 40, containing a predetermined number of viable microorganisms Disposed inside ampule 30 is at least the aqueous component of a nutrient medium for the microorganisms. Disposed inside ampule holder 50a, and either inside or outside of ampule 30, is the non-aqueous component of the nutrient medium. Also disposed inside ampule holder 50a, and either inside or outside of ampule 30, is a growth indicating material, not shown in FIG. 1, which undergoes a visible color change in response to the growth of microorganisms.

When sterility indicator is subjected to a sterilization cycle, the steam or gaseous vapor permeates into the interior cavity of ampule holder 50a through the tortuous paths of gas pervious openings 64, 65, 64a, 65a, gaps 92, 92a, gaps 90 and gaps not shown in FIG. 1 on ribbed portion 88 due to their being rotated about the cylindrical axis with respect to gap 90, thereby subjecting sample strip 40 to the vapor entering from both sides. Upon completion of the sterility cycle, the gas or steam is evacuated or diffuses from the interior cavity through the same tortuous paths in reverse. Ampule 30 is then fractured by turning second annular portion 81 of cap 80 with respect to ampule holder 50a as described above, allowing the nutrient medium to contact the sample strip 40. Alternately, if the liquid in ampule 30 is only the aqueous portion of a nutrient media, it additionally combines with the non-aqueous nutrient portion inside ampule holder 50a to create a complete nutrient medium which contacts sample strip 40. The aqueous nutrient medium is prevented from leaking outside the interior cavity of ampule holder 50a by the tortuous path due to the dimensions of gaps 90 in ribbed portions 86 forming a liquid impervious barrier due to the surface tension of the aqueous nutrient medium, and the liquid tight seal between ribbed portions 86 and grooved regions 62, 62a. Gaps in ribbed portions 88, not shown in FIG. 1, and the liquid impervious seal between grooved regions 63, 63a and ribbed portions 88, provide a backup liquid impervious seal for the liquid disposed in the interior cavity of ampule holder 50a.

The sterility indicator, with the sample strip 40 soaked with aqueous nutrient medium, is subjected to incubation treatment to spur growth in any microorganisms which survive the sterilization cycle. Growth of the microorganisms is indicated by a change in the color of detecting material, which is visible through the translucent walls of ampule holder 50a. A change in color, of course, indicates the sterilization was not successful.

Referring to FIG. 2, ampule holder 50a of the preferred embodiment is shown. Ampule holder 50a is cylindrical having cylindrical wall 53a with inner surface 54a. The ampule holder 50a includes fracture pad 60 extending axially inward from inner surface 54a, grooved regions 62, 63 in inner surface 54a, and gas pervious openings 64, 65 in cylindrical wall 53a.

The half of ampule holder 50a adjacent to open end 66a is a mirror image of the half adjacent to open end 66 about a plane perpendicular to the cylindrical axis at its midpoint, except the half adjacent to open end 66a does not have a protrusion equivalent to fracture pad 60. Specifically, at the half of ampule holder 50a near open end 66a, cylindrical wall 53a has gas pervious openings 64a, 65a opposite one another, and grooved regions 62a, 63a in inner surface 54a of cylindrical wall 53a and extending the complete circumference thereof.

In a representative embodiment of FIG. 2, ampule holder 50a has outer diameter of approximately 8.5 mm, length along its cyclindrical axis of approximately 48 mm, and inner diameter of approximately 7.0 mm.

Referring back to FIG. 1, it is seen that the ampule holder 50a of the sterility indicator 10a receives two caps 80, 80a into each of its open ends 66, 66a. As shown in FIG. 3A, cap 80 has deformable ribbed portions 86, 88 extending circumferentially around first annular portion 84, except for break 90 and similar break on ribbed portion 88, not shown in FIG. 5 due to it being rotated 90° about the cylindrical axis with respect to gap 90. Second annular portion 81 has diameter larger than the inner diameter of cylindrical wall 54a of ampule holder 50a, while first annular portion 84 has outer diameter marginally smaller than inner diameter of cylindrical wall 53a, allowing reception of first annular portion 84 within the interior cavity of ampule holder 50a, by moving it into open end 66 as shown in FIG. 1. Ribbed portions 86, 88 have relatively larger outermost diameter than inner diameter of cylindrical wall; therefore, ribbed portions 86, 88 and/or ampule holder 50a are made of slightly deformable, resilient material to allow complete reception of first annular portion 84 within the interior cavity of ampule holder 50a. When the cap 80 is so disposed, ribbed portions 86, 88 are seated in grooved regions 62, 63. Their relative dimensions are such that complete expansion of the deformed ribbed portion 86, 88 and/or grooved region 62, 63 is not possible, whereby a force results between the cap 80 and the inner surface 54a at the ribbed portion 86, 88 and the grooved region 62, 63 which maintains the cylindrical axis of cap 80 coaxial with that of ampule holder 50a and, consequently, a gap 92 between inner surface 54a and first annular portion 84.

A gas pervious tortuous path exists between the interior cavity of ampule holder 50a and its outside comprising an annular passageway 92, gap 90 in ribbed portion 86, and similar gap, not shown in FIG. 1, on ribbed portion 88, and gas pervious openings 64, 65. The tortuous path is liquid impervious to Tryptic Soy, however, owing to the dimension of gap 90 and a similar gap, not shown in FIG. 1, on ribbed portion 88, which prevents passage due to surface tension and the liquid impervious seal made at the seating of ribbed portions 86, 88 in grooved regions 62, 63.

Figure 3B:
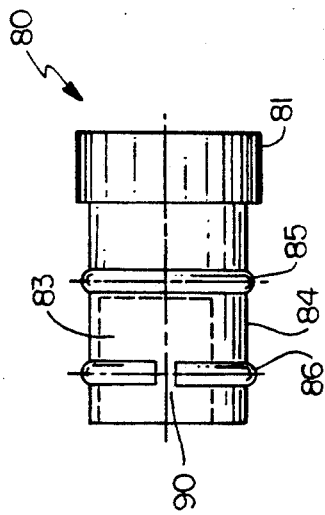
FIG. 3b is a cross-section of the cap of FIG. 4.

Cap 80 may be rotated around its cylindrical axis with respect to ampule holder 50a, by turning second annular portion 81 while maintaining ampule holder 50a fixed. As shown in FIGS. 3A and 3B, first cylindrical portion 84 has bored region 83 which receives one end 32 of ampule 30. Bored region 83 is cylindrical with cylindrical axis parallel to but not coaxial with the cylindrical axis of cap 80, whereby the cylinder comprised of the bored region 83 is eccentrically aligned with the cylinder comprising the outer surface of the first annular portion 84 of cap 80.

Cap 80a which is received in the opposite open end 66a except for one feature described below, and, perhaps, the material of composition, is identical to cap 80. When first cylindrical portion 84 of cap 80a is received in open end 66a, ribbed portions 86, 88 are seated in grooved regions 62a, 63a. The force between the cap 80a and interior surface 54a due to the deformation of ribbed portions 86, 88 and/or grooved regions maintains the cylindrical axis of cap 80a coaxial with that of ampule holder 50a.

The body of cap 80 may be made of rigid, clear pvc and the ampule holder 50a may also be made of clear, translucent, rigid pvc. The ribbed portions 86 88 of the cap 80 are made of deformable material to allow ribbed portions 86, 88 of the cap 80 to be received within the ampule holder 50a as described above, when the dimensions detailed below are used.

Continuing the representative embodiment above, the second annular portion 81 of the cap 80 has diameter of approximately 8.5 mm and length along its cylindrical axis of approximately 3.0 mm. The first annular portion 84 has outer diameter of approximately 6.6 mm and length along the cylindrical axis of approximately 10.0 mm. The gaps 90 in the ribbed portions 86, 88 are 0.1 to 0.2 mm wide to form the requisite liquid impervious barrier to Tryptic Soy.

The bored region 83 of the cap 80 has diameter of approximately 5.7 mm and extends approximately 6.0 mm into the first annular portion 84 measured along the cylindrical axis of the cap 80. The central axis of the bored region 83 is parallel to the central axis of the cap 80, but is separated from it by a distance of approximately 0.5 mm.

Cap 80a is inserted in open end 66a and has essentially identical features to cap 80. Furthermore, when cap 80a is received in open end 66a, an analogous tortuous path exists between the interior and exterior of ampule holder 50a.

Unlike cap 80, cap 80a has bored region 83a with central axis coaxial with the central axis of cap 80a. Therefore, the cylinder comprising bored region 83a is concentrically aligned with the cylinder comprising first annular portion 84.

The ampule 30 is made of frangible glass, although other pressure openable containers may be used. The pressure opening, of course, is accomplished by fracturing the glass. One type of frangible glass is borosilicate onion skin glass. In general, and for the particular embodiments above, ampule impervious and can withstand the temperatures of a steam sterilization cycle.

In the representative embodiment, the ampule 30 has outer diameter of approximately 5.7 mm, length along its cylindrical axis of approximately 40 mm, and wall approximately 0.22 mm thick. The ends 32,33 of the cylindrically shaped ampule may have a rounded contour.

Sample strip 40 is disposed within ampule holder 50a described above. Also disposed within ampule holder 50a, and either inside or outside of ampule 30 is any non-aqueous component of the nutrient medium not found in the aqueous portion disposed in ampule 30, and a growth indicating material, not shown in FIG. 1, which undergoes a visible color change in response to the growth of microorganisms.

The specific dimensions given above for this preferred embodiment are intended to be illustrative and not to limit the invention in any way. The present invention as described in the representative embodiment above and the embodiments below can be applied to sterility indicators and specifically cylindrical sterility indicators of many dimensions. One skilled in the art will be able to extrapolate the appropriate specific dimensions for the features of the present invention for various sizes of the ampule holder and ampule based on the description and specific example above. Similarly, one skilled in the art may extrapolate from the specific example above in constructing a specific device of the embodiments described below.

In another embodiment of the present invention, the sterility indicator is essentially as shown in FIG. 1 and described above. Fracture pad 60 is absent and both bores 83, 83a of both caps 80, 80a are eccentric with respect to the cap. When one cap is rotated with respect to the other, the misalignment of the bores 83, 83a causes their surfaces to exert pressure on the ampule 30, fracturing it.

Figure 4:
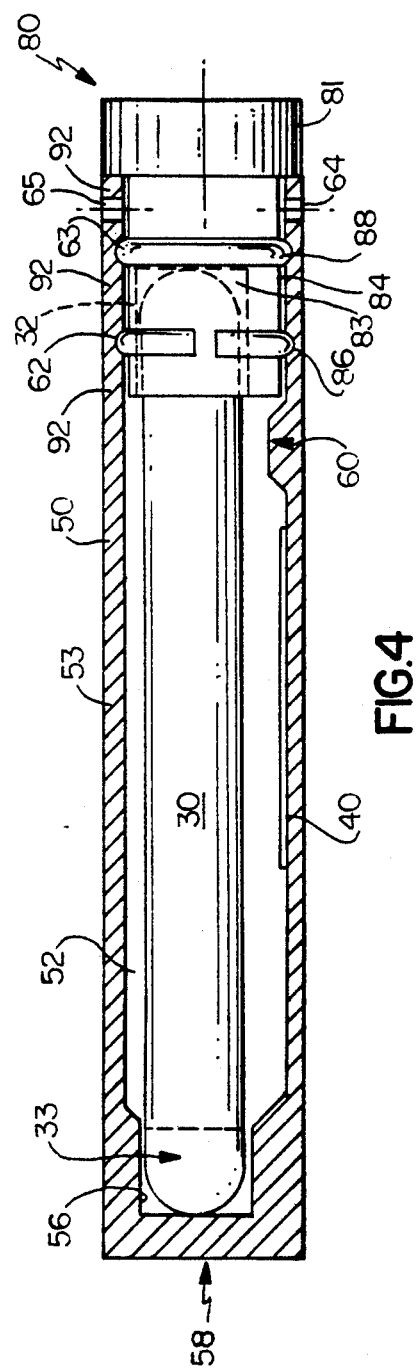
FIG. 4 is a composite cross-sectional and side view of another embodiment of the sterility indicator of the present invention.

In another embodiment of the present invention, shown in FIG. 4, the sterility indicator is very similar to the embodiment of FIG. 1 and described above. The concentrically aligned bored cap has been replaced with an ampule holder 50 of reduced inner diameter at end 58, which supports end 33 of ampule 30 in opening 56. As before, rotation of cap 80 with respect to ampule holder 50 causes ampule 30 to contact fracture pad 60 due to the eccentric bore 83. This fractures ampule 30.

In FIG. 4, the fracture pad 60 could also be removed and ends 32, 33 of ampule 30 could be made to fit snugly inside gap 83 of cap 80 and opening 56 of ampule holder 50. Rotating cap 80 with eccentric bore 83 with respect to ampule holder 50 would torque ampule 30 about its axis, fracturing it.

Note that the embodiments described with respect to FIG. 4 are not preferred embodiments, since only one end of the indicator has a tortuous path, whereas the embodiments described relying on FIG. 1 have tortuous paths at both ends.

The embodiments derived from FIG. 4 are intended for use in a Vacuum-Steam sterilization process. These embodiments would not function as well in a gravity steam or Ethylene Oxide sterilization cycle because without vacuum, and with only one tortuous path it is difficult to replace the air inside the ampule holder with the sterilizing medium. The steam or EO gas would be unable to get in the ampule holder and kill the microorganisms, resulting in a false positive indication.

On the other hand, the embodiments derived from FIG. 1 are well suited for use in a gravity steam or EO cycle. Because there are tortuous paths at both ends of the indicator, diffusion of the steam or EO gas into the ampule holder at one end is facilitated by diffusion of air out of the ampule holder at the other end. Upon completion of the cycle the diffusion of air back into the indicator at one end is facilitated by EO or steam diffusing out at the other end. Thus the conditions inside the indicator follow the cycle and give an accurate indication of the success or failure of the cycle.

Figure 5C:
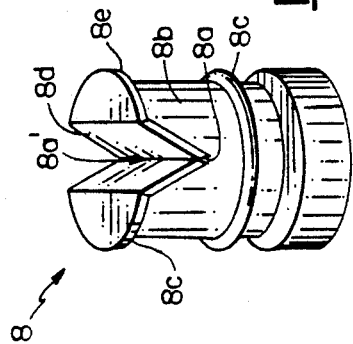
Figure 5A:
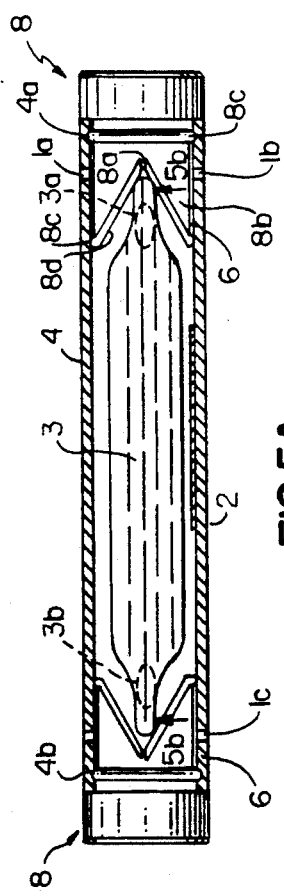
FIG. 5a is a composite cross-sectional and side view of another embodiment of the sterility indicator of the present invention.
Figure 5B:
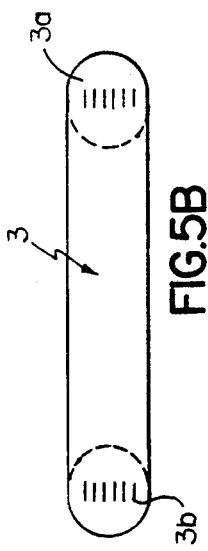

FIGS. 5A, 5B and 5C show another embodiment of the present invention. Ampule holder 4 houses ampule 3 with pinched ends 3a, 3b shown as seen in FIG. 5A. FIG. 5B shows ampule 3 rotated 90° about its central axis from its position in FIG. 5A and demonstrates pinched ends 3a, 3b extend across the diameter of ampule holder 4 in FIG. 1 in a plane perpendicular to the Figure.

Referring to FIGS. 5A and 5C, V-shaped notches 8d of caps 8 support the ampule 3 at pinched ends 3a, 3b when the indicator is assembled. Ribbed portion 8C of cap 8 seat in grooves 4a, 4b of ampule holder 4, and form a liquid impervious seal. Ribbed portion 8c also makes a liquid and gas impervious seal at the inner surface of ampule holder 4. Gas pervious, liquid impervious gap in ribbed portion 8e creates a gas pervious tortuous path between the interior and exterior of ampule holder through gap 8a, annular passageway 6 between cap wall 8b and inner surface of ampule holder 4, and holes 1a, 1b, 1c, 1d.

Rotating one cap with respect to the other causes the notches 8d to torque ampule 3 along its axis at the pinched ends 3a, 3b. This fractures the ampule 3.

The dimensions, features and materials of this embodiment may be adapted from the detailed description above of the FIG. 1 embodiment by one skilled in the art.

Another embodiment similar to that of FIG. 5A would replace one cap with a solid, annually extending closed end of the ampule holder 4, and a ellipsoidal shaped bore therein which receives one of the pinched ends 3a, 3b of ampule 3. This bore would replace the V-shaped notch of the replaced cap, and cooperate to torque ampule 3 when the other cap 8 was rotated with respect to the ampule holder 4.

Figure 6:
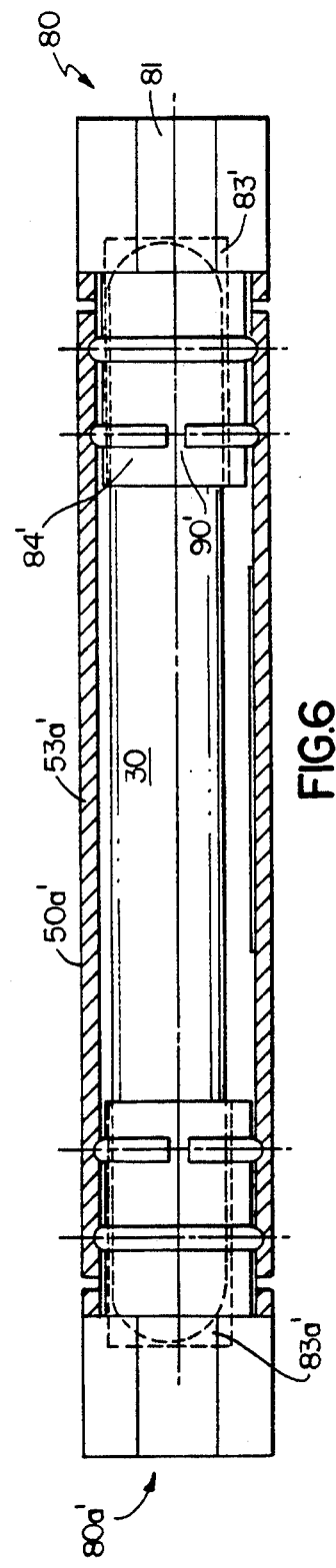
FIG. 6 is a composite cross-sectional and side view of another embodiment of the sterility indicator of the present invention.

Referring to FIG. 6, another embodiment of the present invention is shown similar to the embodiment of FIG. 1. The ampule 30 has the same length of the FIG. 1 embodiment of approximately 40 mm. Ampule holder 53a' however, has a length of approximately 37 mm. Consequently, as shown in FIG. 6, bored region 83' and ampule 30 extend into second annular portion 81' of cap 80'. The same is true of bored region 83' in cap 80' at the opposite end of sterility indicator 50a'. As shown in FIG. 6, the second annular portion 81' of the cap 80' may have an octagonal profile.

The length of the first annular portion 84' of cap 80' is approximately 10 mm while the length of the second annular portion 81' is approximately 8 mm. The length of the bored region is approximately 10 mm and therefore extends approximately 2 mm into the second annular portion 81'. The width of the gap 90' is approximately 0.2 mm.

In FIG. 6 the caps 80', 80a' have eccentrically aligned bores, and the ampule holder 53a' does not have a fracture pad. In this embodiment, when one cap is rotated with respect to the other, the misalignment of the bores 83', 83a' causes their surfaces to exert pressure on the ampule 30, fracturing it.

In another embodiment similar to FIG. 6 but not shown, the ampule holder has a fracture pad as in the FIG. 1 embodiment lying closer to one end of the ampule holder. The cap at the closer end has an eccentrically aligned bore, while the cap at the opposite end has a centrically aligned bore. Rotation of the eccentrically aligned bore causes the ampule to contact and fracture against the fracture pad.

For any of the embodiments above-described, the dimensions of the external profile of the sterility indicator are important. As shown in FIGS. 1, 4, 5A and 6, the external profile of the sterility indicator, i.e., the ampule holder and the portions of the caps not received therein, is cylindrical.

The length of the sterility indicator is 53 to 54 mm long and has diameter between 8.3 mm and 8.6 mm. The external diameter of the ampule holder and the diameter of the portion of the cap not received in the ampule holder is therefore between 8.3 mm and 8.6 mm. The length of the ampule holder is between 37 mm and 48 mm and the length of the unreceived portion of the cap is between 3 mm and 8 mm.

The above description is intended to enable one skilled in the art to practice the present invention according to the inventor's current understanding. It is not intended to limit the scope of the claimed invention.

I claim:

1. A unitary sterility indicator for determining the efficacy of sterilization, comprising:
    (a) an ampule holder with an interior cavity and at least one opening therein, made of translucent and liquid and gas impervious material;
    (b) a closed frangible ampule containing an aqueous nutrient medium, and being pressure openable, said ampule of size allowing its at least partial reception within said interior cavity of said ampule holder through said opening, said ampule being completely disposed within said ampule holder;
    (c) closure means rationally mounted on at least one open end of said ampule holder, said closure means also encompassing any portion of said ampule not received in said ampule holder, said closure means and said ampule holder additionally define a tortuous path opening between the inside and outside of said ampule holder, said tortuous path opening being completely gas transmissive and having at least one point which is liquid impervious;
    (d) a sample medium which carried a predetermined number of microorganisms, said sample medium being disposed in said ampule holder;
    (e) a detector material disposed in said ampule holder and capable of undergoing a visible color change in response to growth of said microorganisms, said color change being visible from outside said ampule holder;
    (f) means for applying a rotational force to said ampule to fracture sand frangible ampule by rotating said closure means;
    whereby said ampule may be opened by the pressure applied from the rotational force thereby exposing said sample medium to said nutrient medium disposed in said ampule.

2. An indicator as in claim 1 wherein said ampule holder is a hollow cylinder with cylinder walls of concentric inner and outer surfaces, and at least one open end.

3. An indicator as in claim 1 wherein said ampule is cylindrically shaped with an interior cavity and thin walls of outer diameter smaller than the inner diameter of said ampule holder.

4. An indicator as in claim 3 wherein said closure means for said at least one open end of said ampule holder is a rotatable cap.

5. An indicator as in claim 4 wherein aid cap is solid and cylindrical, and further includes a first annular portion which extends into said ampule holder, and receives said frangible ampule within.

6. An indicator as in claim 5 wherein the surface of said deformable first annular portion of said cap has at least one deformable and concentric ribbed portion of outer diameter greater than the inner diameter of said ampule holder, whereby a force is exerted between said at least one ribbed portion and said inner surface of said ampule holder when said first annular portion of said cap is received in said ampule holder.

7. An indicator as in claim 6 wherein the portion of the inner surface of said ampule holder which receives said first annular portion of said cap has at least one concentric groove which receives said at least one ribbed portion of said cap when said cap is received in said ampule holder, whereby said at least one ribbed portion received in said at least one grooved portion forms a liquid impervious seal between said cap and the inner surface of said ampule holder, while allowing rotation between said cap and said ampule holder.

8. The indicator according to claim 7 wherein said at least one ribbed portion of said cap has a liquid impervious, gas pervious gap defined therein whereby a gas pervious, liquid impervious tortuous path is formed in the annular passageway between said first annular portion of said cap and the inner surface of said ampule holder.

9. The indicator according to claim 8 wherein there are two ribbed portions with said gaps separated by 90° along the center axis of said cap.

10. The indicator according to claim 9 wherein at least said first annular portion of said cap has a bored region of cylindrical shape which receives one end of said ampule when said first annular portion of aid cap is received in said ampule holder.

11. The indicator according to claim 1 wherein said sample medium is a dry sample strip with a predetermined number of viable microorganism disposed thereon, which grow when placed in contact with an aqueous nutrient medium.

12. A sterility indicator as in claim 4 wherein said ampule holder has two open ends, with each of said open ends closed by caps.

13. A sterility indicator as in claim 12 wherein one of said caps has a centrically aligned bore with respect to the central axis of said cap and other other of said caps has eccentrically aligned bore with respect to the central axis of said first cap, said bores receiving and supporting opposite ends of said ampule disposed within said ampule holder.

14. A sterility indicator as in claim 1 wherein said closure means defines an eccentrically aligned bore with respect to the axis of rotation o the closure means, said bore receiving and supporting an end portion of said ampule holder.

15. A sterility indicator as in claim 14 wherein said means for applying a rotational force for fracturing said ampule includes a fracture pad on an inner surface of the ampule holder extending inward toward the cylindrical axis of said ampule holder, whereby rotational of said closure means with said eccentrically aligned bore causes said ampule to fracture on said pad.

16. A sterility indicator as in claim 12 wherein said means for applying a rotational force for fracturing said ampule includes said caps having eccentrically aligned bore, said bores receiving and supporting opposite ends of said ampule disposed within said ampule holder, such that rotation of said caps with respect to one another applies a fracture force on said ampule at the points of contact with said bores.

17. A sterility indicator as in claim 1 wherein said ampule holder has one closed end and an adjacent first annular portion of reduced inner diameter with respect to a second annular portion and an open end closed by one cap.

18. a sterility indicator as in claim 17 wherein said one cap defines an eccentrically aligned bore, said bore and said first annular portion receiving and supporting opposite ends of said ampule disposed within said ampule holder.

19. A sterility indicator as in claim 18 wherein said means for applying a rotational force for fracturing said ampule includes a fracture pad on an inner surface of the ampule holder which extends inward toward the cylindrical axis of said ampule holder such that rotation of said cap with said eccentrically aligned bore causes said ampule to contact said fracture pad and fracture.

20. A sterility indicator as in claim 1 wherein said unitary sterility indicator has a total length between 53 mm and 54 mm and an outer diameter between 8.3 mm and 8.6 mm.

21. A sterility indicator as in claim 1 wherein aid ampule holder is made of void translucent polyvinylchloride.

22. A sterility indicator as in claim 1 wherein aid closure means is made of rigid polyvinylchloride with a deformable ribbed inner annular portion which engages said ampule holder.

23. A unitary sterility indicator for determining the efficacy of sterilization comprising:
(a) a cylindrical ampule holder with both ends open, made of translucent and liquid and gas impervious material;
(b) a closed ampule containing an aqueous nutrient medium, made of frangible glass, said ampule of size allowing its at least partial reception within an interior cavity of said ampule holder through one of both of said open ends,
(c) caps of closing said open ends of said ampule holder, said caps having sealing means which prevent liquid from passing between the interior and exterior of the ampule holder, said caps encompassing any portion of said ampule not received in said ampule holder;
(d) said ampule holder and each of said caps defining a gas pervious liquid impervious tortuous path between the interior and exterior of the sad ampule holder;
(e) said caps being rotatable with respect to said ampule holder and each other about the cylindrical axis of said ampule holder;
(f) first means for mounting said ampule within said caps such that rotation of one or more of said caps causes said ampule to rotate within said ampule holder;
(g) second means for preventing rotation of said ampule; whereby rotation of aid one or more caps causes rotation of said ampule and fracture of said frangible glass by rotational force.

24. A sterility indicator as in claim 23 wherein said caps receive at least a portion of opposite ends of said ampule.

25. A sterility indicator as in claim 24 wherein said ampule has inched ends and said caps define notches for receiving said pinched ends.

26. A sterility indicator as in claim 25 which further includes a fracture pad extending from an inner surface of said ampule holder, and at least one cap which defines an eccentrically aligned bore such that, when rotated, said ampule contacts said fracture pad.

27. A sterility indicator as in claim 26 wherein said bores are eccentrically aligned and the force applied by the said ampule is fractured by bores on said ampule when said caps are rotated with respect to one another.

28. A unitary sterility indicator for determining the efficacy of sterilization comprising:
(a) a cylindrical ampule holder with both ends open, made of translucent and liquid and gas impervious material;
(b) a closed ampule with pinched ends containing an aqueous nutrient medium, made of frangible glass, said ampule disposed within said ampule holder;
(c) caps for closing said open ends of said ampule holder and engaging said pinched ends, said caps including sealing means which prevent liquid from passing between the interior and extenor of the ampule holder;
(d) said caps and said ampule holder defining a gas pervious liquid impervious tortuous path between the interior and exterior of said ampule holder;
(e) said caps being rotatable with respect to said ampule holder and each other about the cylindrical axis of said ampule holder;
whereby rotation of one cap with respect to the other applies a twisting force to said ampule at said pinched ends, thereby fracturing said ampule.

29. A unitary sterility indicator for determining the efficacy of sterilization, comprising:
(a) an ampule holder with an interior cavity and having two open ends therein, made of translucent and liquid and gas impervious material;
(b) a closed frangible ampule containing an aqueous nutrient medium, and being pressure openable, said ampule of said allowing its at leas partial reception within said interior cavity of said ampule holder through said open ends, said ampule being completely disposed within said ampule holder;
(c) a closure member rotationally mounted on each of said open ends of said ampule holder, said closure member also encompassing any portion of said ampule not received in said ampule holder, and defining a gas pervious, liquid impervious path between said closure member and said ampule holder at each end thereof;

(d) a sample medium which carries a predetermined number of microorganisms, said sample medium being disposed in said ampule holder;

(e) a detector material disposed in said ampule holder and capable of undergoing a visible color change in response to growth of said microorganisms, said color change being visible from outside said ampule holder;

(f) means for preventing rotation of the ampule to fracture said frangible ampule with rotational force when said closure means is rotated;

whereby said ampule may be opened by the pressure amplified from the rotational force thereby exposing said sample medium to said nutrient medium disposed in said ampule.

30. An indicator as in claim 29 wherein said ampule holder is a hollow cylinder with a cylindrical wall of concentric inner and outer surfaces having an inner diameter and two open ends.

31. An indicator as in claim 30 wherein said ampule is cylindrically shaped with an interior cavity and frangible wall having an outer diameter smaller than the inner diameter of said ampule holder.

32. An indicator as in claim 31 wherein said closure member for each of said open ends of said ampule holder is a rotatable cap.

33. A unitary sterility indicator for determining the efficacy of sterilization, comprising:

(a) an ampule holder with an interior cavity and having two open ends therein, made of translucent and liquid and gas impervious material;

(b) a closed frangible ampule containing an aqueous nutrient medium, said ampule of a size allowing its at least partial reception within said interior cavity of said ampule holder through an open end thereof;

(c) closure means rotationally mounted on each of said open ends of said ampule holder, said closure means also encompassing any potion of sad ampule not received in said ampule holder, and defining a gas pervious, liquid impervious path between said closure means and aid ampule holder at each end thereof;

(d) a sample medium carries a predetermined number of microorganisms, said sample medium being disposed in said ampule holder;

(e) a detector material disposed in said ampule holder and capable of undergoing a visible color change in response to growth of said microorganisms, said color change being visible from outside said ampule holder;

(f) means for fracturing said frangible ampule by rotation of said closure means;

whereby said ampule may be opened by the pressure applied from the rotation of the closure means thereby exposing said sample medium to said nutrient medium disposed in said ampule.

* * * * *

UNITED STATES PATENT AND TRADEMARK OFFICE
CERTIFICATE OF CORRECTION

PATENT NO. : 5,167,923
DATED : December 1, 1992
INVENTOR(S) : Pim Van Iperen

It is certified that error appears in the above-identified patent and that said Letters Patent is hereby corrected as shown below:

On the Title Page, Section [57]: delete Abstract and insert the following new Abstract. --A sterility indicator for use in hospitals and laboratories. The device uses a cylindrical ampule holder with an ampule containing nutrient media and spore strip disposed therein. One or more gas pervious, liquid impervious tortuous paths lie between the interior and exterior of the ampule holder. The ampule is closed at one or both ends by a rotatable cap, at least one of which engages the ampule for rotation. Fracturing of the ampule may be accomplished by rotation of the rotatable cap, which rotate the ampule, which is fixed at the other end, or rotated into a fracture pad by way of eccentric rotation.--

Column 1, line 36: after "successful" insert --.--
Column 1, line 45: after "methods" insert --.--
Column 2, line 9: after "reside" insert --on spore strips with $10^5$ or more spores. For EO indicators,--
Column 2, line 29: after "broth" insert --.--
Column 2, line 43: after "plastic" insert --.--
Column 3, line 37: after "fracture" insert --.--
Column 3, line 39: after "problem" insert --.--

UNITED STATES PATENT AND TRADEMARK OFFICE
CERTIFICATE OF CORRECTION

PATENT NO. : 5,167,923
DATED : December 1, 1992
INVENTOR(S) : Pim Van Iperen

It is certified that error appears in the above-identified patent and that said Letters Patent is hereby corrected as shown below:

Column 6, line 50: after "microorganisms insert --.--

Column 9, line 16: after "ampule" insert --holder 50a, ampule 30 and caps 80, 80a are gas and liquid--

Column 11, line 55, Claim 1: "rationally" should read --rotationally--

Column 12, line 12, Claim 2: "cylinder" (2nd occur.) should read --cylindrical--

Column 12, line 22, Claim 5: "aid" should read --said--

Column 12, line 57, Claim 10: "aid" should read --said--

Column 12, line 61, Claim 11: "microorganism" should read --microorganisms--

Column 13, line 1, Claim 13: delete second occurrence of "other"

Column 13, line 8, Claim 14: "o" should read --of--

Column 13, line 32, Claim 18: "a" should read --A--

Column 13, line 48, Claim 21: "aid" should read --said--

UNITED STATES PATENT AND TRADEMARK OFFICE
CERTIFICATE OF CORRECTION

PATENT NO. : 5,167,923

DATED : December 1, 1992

INVENTOR(S) : Pim Van Iperen

It is certified that error appears in the above-identified patent and that said Letters Patent is hereby corrected as shown below:

Column 13, line 51, Claim 22: "aid" should read --said--

Column 13, line 64, Claim 23: "of both" should read --or both--

Column 14, line 5, Claim 23: "sad" should read --said--

Column 14, line 15, Claim 23: "aid" should read --said--

Column 14, line 22, Claim 25: "inched" should read --pinched--

Column 14, line 29, Claim 27: "said" should read --the--

Column 14, line 44, Claim 28: "extenor" should read --exterior--

Column 14, line 62, Claim 29: "said" should read --size--

Column 14, line 62, Claim 29: "leas" should read --least--

Column 15, line 18, Claim 29: "amplified" should read --applied--

UNITED STATES PATENT AND TRADEMARK OFFICE
CERTIFICATE OF CORRECTION

PATENT NO. : 5,167,923

DATED : December 1, 1992

INVENTOR(S) : Pim Van Iperen

It is certified that error appears in the above-identified patent and that said Letters Patent is hereby corrected as shown below:

Column 16, line 12, Claim 33: "potion of sad" should read --portion of said--

Column 16, line 15, Claim 33: "aid" should read --said--

Column 16, line 17, Claim 33: after "medium" insert --which--

Column 13, line 1, after "and" insert --the--.

Column 14, line 5, delete "the" (2nd occur.).

Signed and Sealed this

Eleventh Day of January, 1994

Attest:

BRUCE LEHMAN

*Attesting Officer*   *Commissioner of Patents and Trademarks*